US008983653B2

(12) United States Patent
Barrett et al.

(10) Patent No.: US 8,983,653 B2
(45) Date of Patent: Mar. 17, 2015

(54) ELECTROMECHANICAL LATCH AND EJECTOR

(75) Inventors: John Todd Barrett, Madison, MS (US); Fred P. Schoville, Brighton, MI (US)

(73) Assignee: Advantage Pharmacy Services LLC, Madison, MS (US)

( * ) Notice: Subject to any disclaimer, the term of this patent is extended or adjusted under 35 U.S.C. 154(b) by 67 days.

(21) Appl. No.: 13/526,807

(22) Filed: Jun. 19, 2012

(65) Prior Publication Data

US 2013/0018505 A1 Jan. 17, 2013

Related U.S. Application Data

(60) Provisional application No. 61/508,225, filed on Jul. 15, 2011.

(51) Int. Cl.
*G06F 17/00* (2006.01)
*B65G 59/00* (2006.01)
*A61G 12/00* (2006.01)

(52) U.S. Cl.
CPC .................................. *A61G 12/001* (2013.01)
USPC ........................... 700/237; 700/242; 700/243

(58) Field of Classification Search
CPC ................................................... A61G 12/001
USPC .......................................... 700/237, 242, 243
See application file for complete search history.

(56) References Cited

U.S. PATENT DOCUMENTS

| | | | | |
|---|---|---|---|---|
| 3,869,064 A * | 3/1975 | Payne | ............................. | 221/19 |
| 4,000,800 A * | 1/1977 | Loucks, Sr. | ................... | 194/215 |
| 4,209,111 A | 6/1980 | Lotspeich et al. | | |
| 4,221,376 A * | 9/1980 | Handen et al. | ................ | 271/149 |
| 4,429,639 A * | 2/1984 | Burchart | ........................ | 109/19 |
| 5,940,306 A * | 8/1999 | Gardner et al. | ............... | 700/244 |
| 6,003,008 A * | 12/1999 | Postrel et al. | ...................... | 705/4 |
| 6,412,654 B1 * | 7/2002 | Cleeve | ............................. | 221/7 |
| 6,511,138 B1 | 1/2003 | Gardner et al. | | |
| 7,602,135 B2 * | 10/2009 | Huber et al. | .................. | 318/651 |
| 7,668,620 B2 | 2/2010 | Shoenfeld | | |
| 7,896,149 B2 * | 3/2011 | Tabata et al. | .................. | 194/302 |
| 8,234,008 B2 * | 7/2012 | Weber | ........................... | 700/242 |
| 8,662,606 B2 * | 3/2014 | Santmyer et al. | ........... | 312/319.7 |
| 2002/0165641 A1 * | 11/2002 | Manalang et al. | ............. | 700/237 |
| 2009/0118860 A9 * | 5/2009 | Sjostrom | ....................... | 700/231 |
| 2010/0106291 A1 * | 4/2010 | Campbell et al. | ............. | 700/231 |
| 2010/0114367 A1 | 5/2010 | Barrett et al. | | |
| 2010/0308704 A1 | 12/2010 | Rahilly | | |
| 2013/0018505 A1 * | 1/2013 | Barrett et al. | .................. | 700/231 |
| 2013/0331983 A1 * | 12/2013 | Barrett et al. | .................. | 700/236 |

* cited by examiner

*Primary Examiner* — Michael K Collins
(74) *Attorney, Agent, or Firm* — Reising Ethington P.C.

(57) ABSTRACT

An electromechanical latch and ejector to selectively unlatch and eject an object.

29 Claims, 7 Drawing Sheets

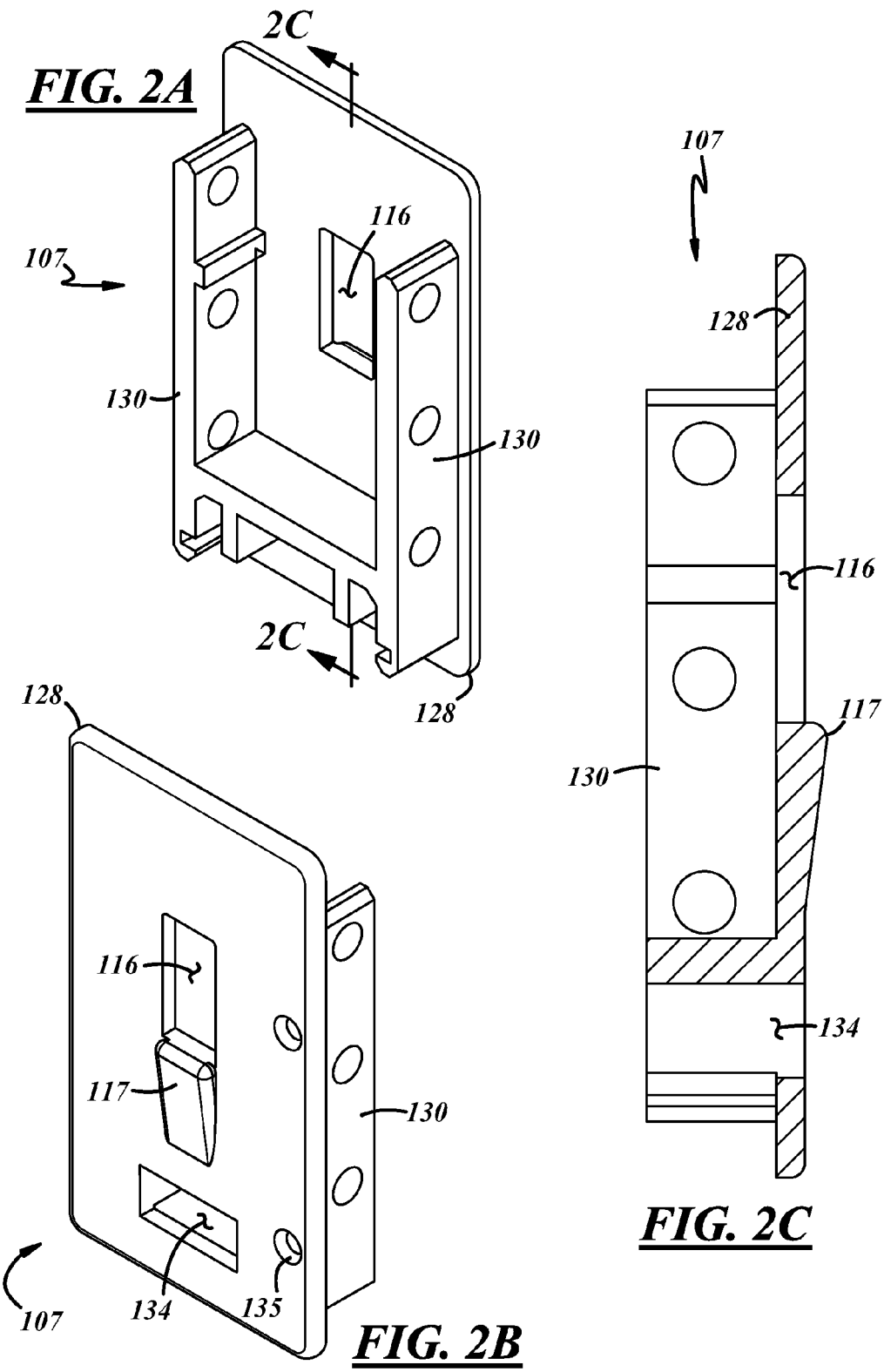

ELECTROMECHANICAL LATCH AND EJECTOR

CROSS-REFERENCE TO RELATED APPLICATION

This application claims the benefit of U.S. Provisional Application No. 61/508,225, filed Jul. 15, 2011, the content of which is incorporated herein by reference in its entirety.

TECHNICAL FIELD

The field to which the disclosure generally relates includes electromechanical latches.

BACKGROUND

Electromechanical latches have many uses, for example, to latch drawers to cabinets. Conventional latches typically include complex mechanical parts and kinematics, and costly electrical devices and configurations. Also, although conventional latches may be used to latch and unlatch objects, they are not used to eject the objects.

BRIEF SUMMARY

The present disclosure is directed to an electromechanical latch and ejector to selectively unlatch and eject an object.

BRIEF DESCRIPTION OF THE DRAWINGS

Illustrative embodiments of the invention will become more fully understood from the detailed description and the accompanying drawings, wherein:

FIG. 2A is a front perspective view of a rear cover for the drawer of FIG. 2;

FIG. 2B is a rear perspective view of the rear cover of FIG. 2A;

FIG. 2C is a sectional side view of the rear cover of FIG. 2A, taken along line 2C-2C from FIG. 2A;

DETAILED DESCRIPTION OF ILLUSTRATIVE EMBODIMENTS

The following description of the embodiment(s) is merely illustrative in nature and is in no way intended to limit the invention, its application, or uses.

Figure 1:
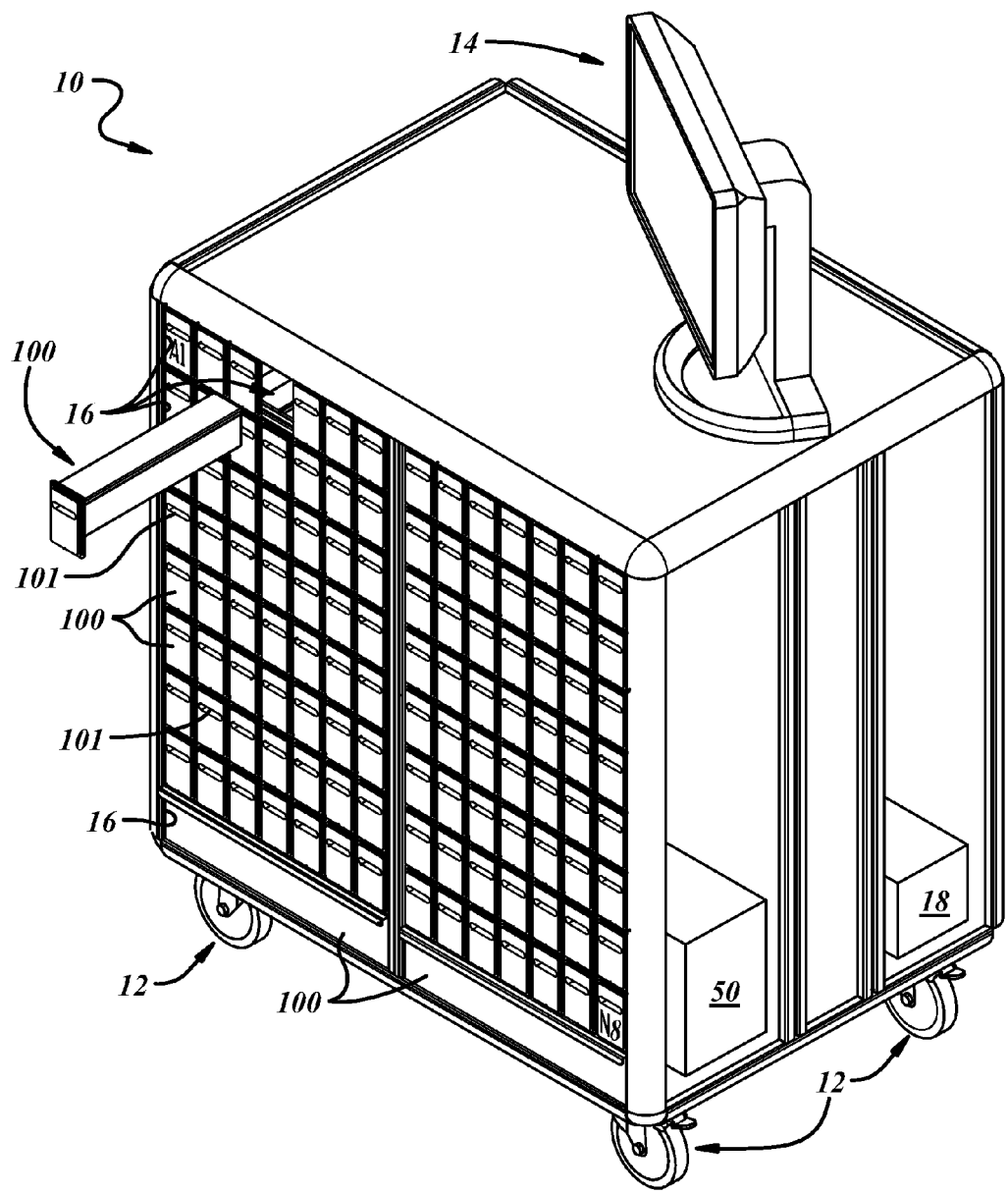
FIG. 1 is a perspective view of an apparatus according to one illustrative embodiment, and illustrating a drawer exploded out of a corresponding compartment.

FIG. 1 illustrates an apparatus 10, which, according to an example embodiment, may include a mobile, computerized, medication administering cart, as shown. For example, a plurality of wheels 12 may be mounted to the apparatus 10 to permit transport of the apparatus 10 from room to room by a medication administering attendant while making patient rounds. In another embodiment, the apparatus 10 may be stationary, for example, built into a workstation, cabinet, desk, or the like in any suitable facility. Also, the apparatus 10 may include a touch screen monitor 14 mounted on the apparatus 10 for easy access and view by the attendant. The touch screen monitor 14 may be further equipped with a conventional mouse or keyboard or replaced with a conventional monitor equipped with a conventional mouse or keyboard. Further, the apparatus 10 may include a cabinet or housing (either for the mobile cart or the stationary apparatus embodiments) including a plurality of compartments 16 for receiving cassettes or drawers 100 that may be used to store medication, bandages and other types of medical supplies as well as other medications that cannot be easily packaged such as medications in liquid form, creams, lotions, powders, etc. for administering to a patient. For security purposes, such drawers 100 may be locked or latched.

The drawers 100 may be arranged in the apparatus 10 in an array, as shown, or in any other suitable arrangement. In an array, the drawers 100 may be identified by column and row. For example, as shown in FIG. 1, there are eight rows and fourteen columns that may be identified alphanumerically. For instance, the rows may be identified as rows A through N and the columns may be identified as columns one through eight. As used herein, the term "drawer" includes any suitable device or component that may be slid into and out of another apparatus, for example, a cabinet, cart, or the like.

The apparatus 10 also may include a computer 50 and one or more batteries 18 for powering the computer 50, drawers 100, EEPROM, release mechanisms, and any other powered elements of the apparatus 10. Of course, the apparatus 10 may be supplied with power in any other suitable manner, including AC utility or generator power, or the like.

Figure 2:
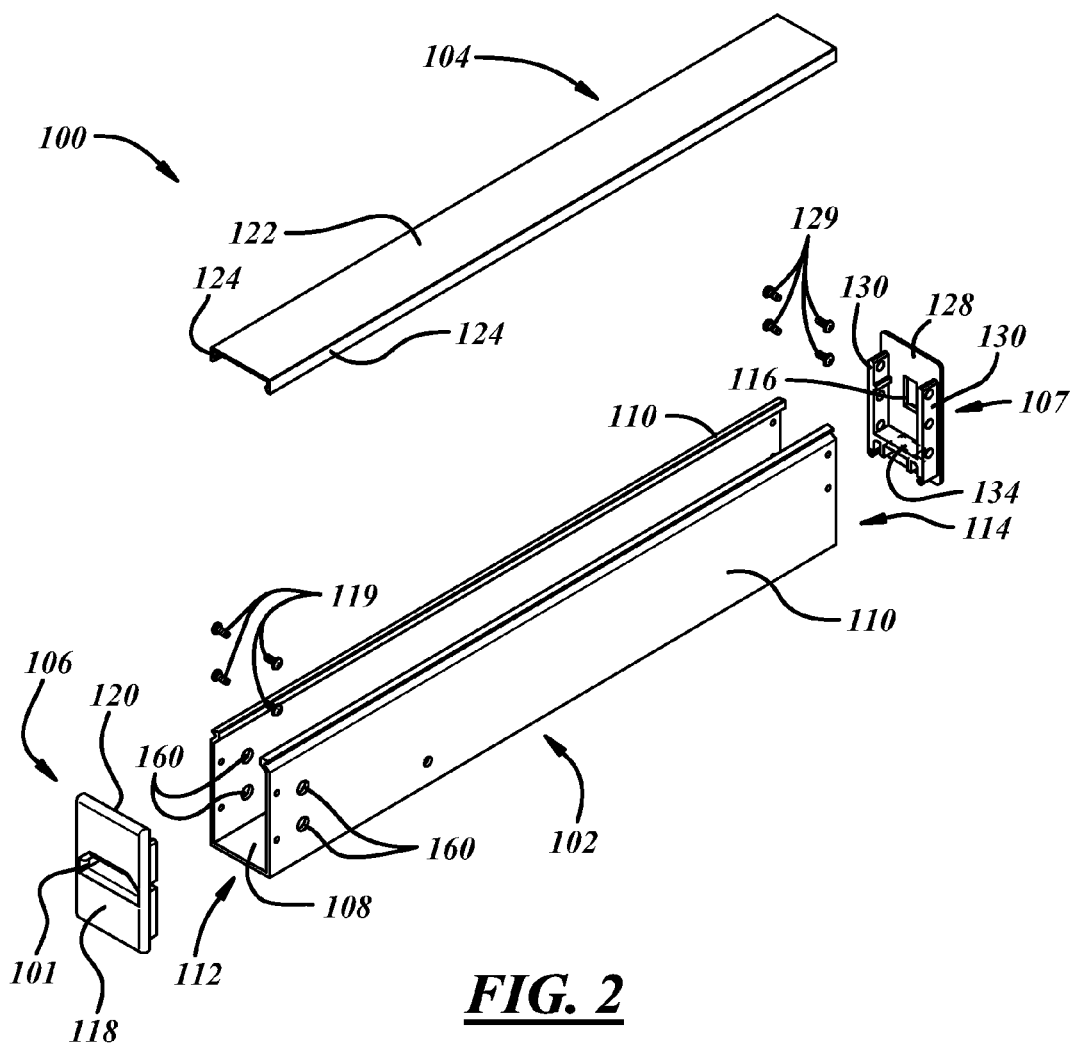
FIG. 2 is an exploded perspective view of an illustrative embodiment of the drawer of the apparatus of FIG. 1.

In a particular example illustrated in FIG. 2, the illustrative drawer 100 includes a housing that may be comprised of a main body 102 to provide support for other portions of the drawer 100, a top cover 104 that covers the main body 102, and a front cover 106 that frontally covers the main body 102 and includes an outlet 101, for example a slit, through which medication may be conveyed, and a rear cover 107 that covers a rearward end of the main body 102. The main body 102 includes a base 108, sides 110 extending from the base 108, a front 112 to which the front cover 106 is coupled in any suitable manner, and a rear 114. The main body 102 may be a drawer base identifiable by part number FS1.5x3LG6NM available from PANDUIT of Tinley Park, Ill., or may be custom molded, for example, using ALUMILITE brand molds and techniques, or may be constructed and arranged in any other suitable manner from any other suitable materials.

The top cover 104 includes a top base 122 and flanges 124 extending therefrom, wherein the top cover 104 is coupled to the main body 102 in any suitable manner. For example, the sides 110 of the main body 102 may be frictionally engaged to the flanges 124 of the top cover, or the sides 110 of the main body 102 may be frictionally slidably interengaged to the flanges 124 of the top cover 104. The top cover 104 may be identifiable as part number C1.5LG6 available from PANDUIT of Tinley Park, Ill. The top cover 104 also may be custom molded, for example, using ALUMILITE brand molds and techniques.

The front cover 106 includes a front portion 118, a rear portion 120 coupled to the main body 102, and the outlet 101 extending therethrough. The front cover 106 may include flanges 121 extending from the rear portion 120 for coupling to the sides 110 of the main body 102 in any suitable manner, for example via fasteners 119.

Referring to FIGS. 2A through 2C, the rear cover 107 may include a base 128, and flanges 130 extending from the base 128 for coupling to the sides 110 of the main body 102 of the drawer housing in any suitable manner for example via frictional fit, fasteners 129 or the like. The rear cover 107 may include a latch aperture 116, a connector passage 134 that may extend through the base 128, and a guide pin passage 135 (FIG. 2C). The rear cover 102 also may include a cam surface 117 extending from the base 128 and arranged adjacent a lower portion of the aperture 116.

Figure 3:
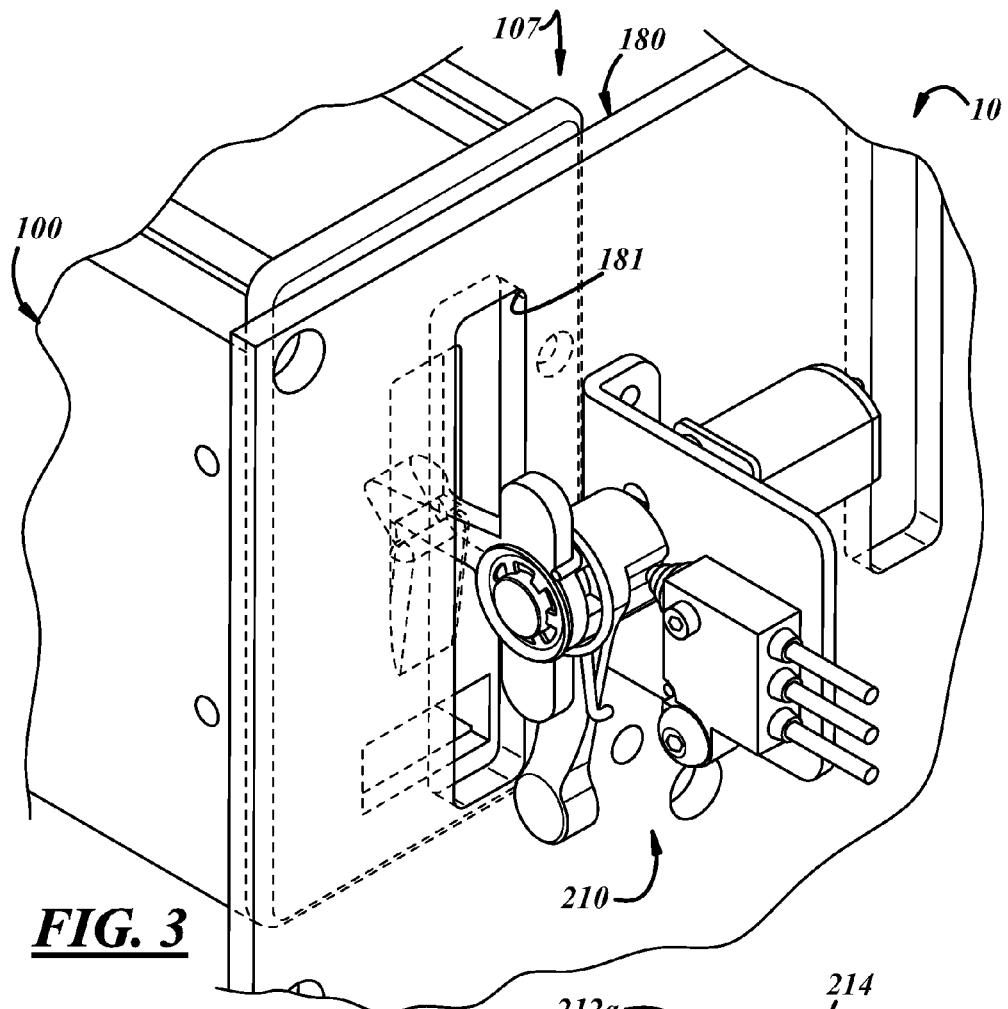
FIG. 3 is a perspective view of an illustrative embodiment of an electromechanical latch and ejector that may be used to selectively unlatch and eject the drawer of FIG. 2 with respect to a backplane of the apparatus of FIG. 1.

As shown in FIG. 3, a backplane 180 may be coupled in any suitable manner to the apparatus 10, and an electromechanical latch and ejector 210 may be coupled to the backplane 180 to selectively couple the drawer 100 to the apparatus 10. The backplane 180 may include one or more circuit boards that may be coupled, for example, to structural members or internal framework of the housing of the apparatus 10. The backplane 180 may include a backplane aperture 181 to allow one or more portions of the latch and ejector 210 to extend therethrough as will be described in further detail below. Although not shown, any suitable hard stops may be provided between the drawer 100 and the framework of the apparatus housing to prevent the drawer 100 from damaging the backplane 180, for example, in the event that the drawer 100 is slammed to its closed position.

Figure 4:
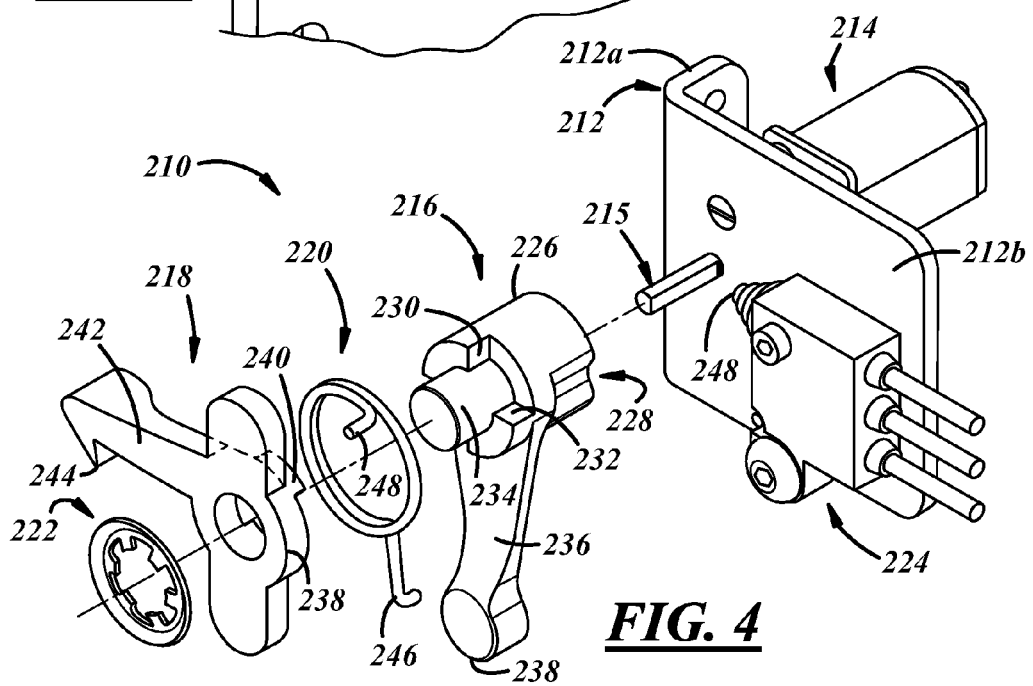
FIG. 4 is an exploded perspective view of the latch of FIG. 3.

Referring to FIG. 4, the electromechanical latch and ejector 210 may include a bracket 212 for mechanical coupling to the backplane 180 (FIG. 3) in any suitable manner, for example, with pins, clips, fasteners, or the like. The latch and ejector 210 also includes an electrical actuator 214 to produce revolutionary rotational motion, an ejector member 216 operatively coupled, directly or indirectly, to the actuator 214 for revolutionary rotation, and a latch member 218 operatively coupled, directly or indirectly, in a pivotable manner with respect to the actuator 214 and coupled, directly or indirectly, to the ejector member 216 via a rotary lost motion connection. The ejector member 216 may be rotationally fixed with respect to the actuator 214. The latch and ejector 210 also may include a spring 220 operatively coupled to the ejector member 216 and the latch member 218 to bias the latch member 218 to a normal latch position with respect to the ejector member 216, and a fastener 222 to retain the latch member 218. The latch and ejector 210 further may include a sensor 224 operatively coupled to the ejector member 216 to provide an indication of a rotational position of the ejector member 216. In other embodiments, the sensor 224 instead may be operatively coupled to at least one of the actuator 214 or the latch member 218 to provide an indication of a rotational position thereof.

The bracket 212 may have a first flange 212a coupled to the backplane 180 (FIG. 3) in any suitable manner, and a second flange 212b wherein the actuator 214 or a portion thereof is carried by the bracket 212 on one side of the second flange 212b, and the ejector member 216 and latch member 218 are disposed on another side of the second flange 212b.

The actuator 214 may include a powertrain, which in one embodiment includes an electrical motor, and in another embodiment also may include a drivetrain coupled to the motor. The drivetrain may include a gearbox, belt and pulley reducer, or the like, or any other suitable type of speed reducer. In any case, the motor may be powered and controlled in any suitable manner and may be electrically coupled to the backplane 180 in any suitable manner. For example, the powertrain may include a GM 10 geared pager motor product available from Solarbotics of Calgary, Canada. The actuator 214 may be coupled to the bracket 212 by fasteners, pins, clips, or the like, or in any other suitable manner. In any event, the actuator 214 includes an output shaft 215 that may extend through the bracket 212, for example, through the second flange 212b.

The ejector member 216 may include an ejector hub 226 that may be coupled to the output shaft 215 of the actuator 214 in any suitable manner, for example, via an interference fit and cooperating flats. The hub 226 may include a rotational position reference 228, which may in the form of a detent, for cooperating with a portion of the sensor 224 as will be described herein below. The ejector member 216 also may have angularly spaced stops 230, 232 with an angular space therebetween for receiving a portion of the latch member 218 as will be described herein below. The ejector member 216 further may include a shaft portion 234 for carrying a portion of the latch member 218 as will be described herein below. Moreover, the ejector member 216 may include an ejector arm 236 that extends radially outwardly from the ejector hub 226 and terminates in an end 238 that may be rounded for cooperation with the drawer 100 (FIG. 3) as will be described herein below.

The latch member 218 may include a latch hub 238 that may be disposed generally axially adjacent to the ejector hub 226 and rotatably carried on the shaft portion 234 thereof. The latch member 218 also may include a projection 240 axially extending from the latch hub 238 and disposed in the angular space between the stops 230, 232 of the ejector member 216. The latch member 218 further may include a latch arm 242 extending radially outwardly from the latch hub 238 and having a bayonet end with a barb 244.

Still referring to FIG. 4, the spring 220 may be operatively coupled to and between the ejector and latch members 216, 218 to bias the latch member 218 to a normal latch position with respect to the ejector member 216. The spring 220 may be a coiled, torsional spring having one end 246 engaged to the ejector member 216 and another end 248 engaged to the latch member 218 in any suitable manner. Any other suitable spring arrangements may be used to bias the latch member 218 toward its normal latch position with respect to the ejector member 216.

Accordingly, the latch member 218 may be coupled with respect to the ejector member 216 via a rotary lost motion connection. In other words, the ejector member 216 may be rotationally fixed with respect to the actuator output shaft 215, and the latch member 218 may be pivotable with respect to the actuator output shaft 215.

The fastener 222 may be a retaining nut, speed nut, tinnerman nut, clip, or any other suitable fastener. The fastener 222 may be coupled to the end of the shaft portion 234 of the ejector member 216, for example, by pressing, staking, or the like.

The sensor 224 may be electromechanical and may include a translatable plunger 248 to cooperate with the positional reference 228 of the ejector member 216. The sensor 224 may be coupled to the bracket 212 by clips, pins, fasteners, or the like, or in any other suitable manner. Also, the sensor 224 may be disposed on the same side of the second flange 212b of the bracket 212 as the ejector and latch members 216, 218. The sensor 224 may be electrically coupled in any suitable manner to one or both of the actuator 214 and/or the computer 50 (FIG. 1), either directly, or indirectly via the backplane 180 or in any other suitable manner.

Figure 5:
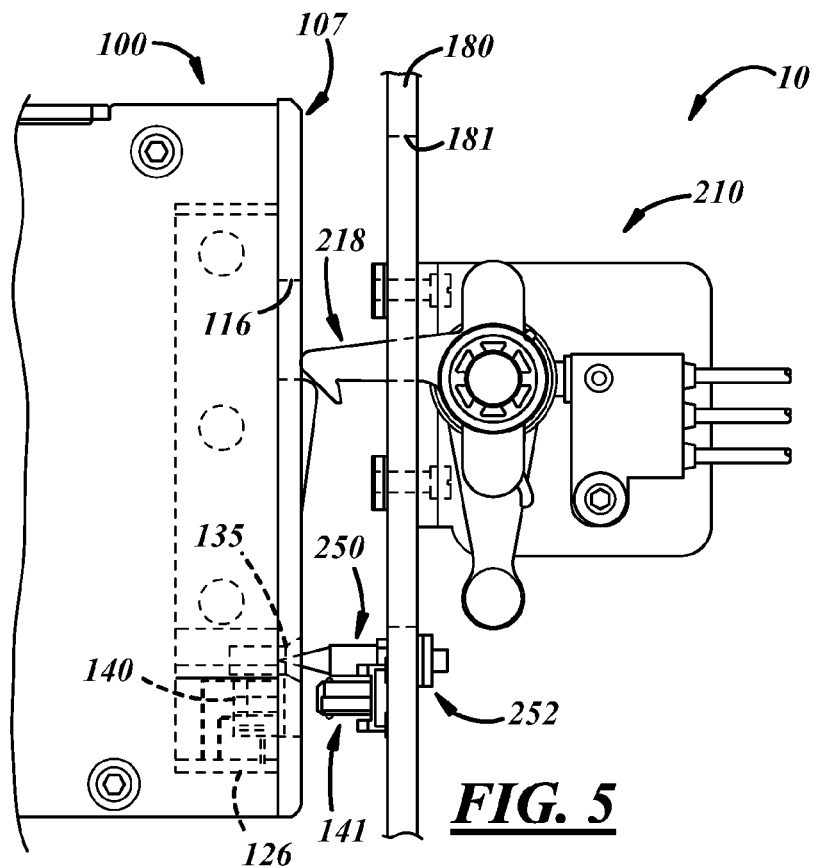
FIG. 5 is a fragmentary side view of a portion of the apparatus of FIG. 1, illustrating the electromechanical latch and ejector of FIG. 3 in an initial engagement position with a rear portion of one of the drawers of FIG. 1.

Referring now to FIG. 5, each drawer 100 may include an electrical connector 140 that may be coupled to and carried by a circuit board 126 in any suitable manner, for example, by soldered pins. In turn, the circuit board 126 may be carried by the housing of the drawer in any suitable manner. Likewise, the apparatus 10 also may include an electrical connector 141 that may be coupled to the backplane 180 in any suitable manner, for example, by soldered pins. The connector 141 may be the counterpart connector for the drawer connector 140 and, for example, also may be from FCI of Versailles Codex, France. The connectors 140 and 141 are coupled to their respective supports such that they align and engage with one another. The connectors 140, 141 may be 10 pin connectors, and one or both may incorporate a floating insertion feature that allows a male end of the connector(s) to float horizontally and vertically making insertion easier. Of course, although not shown in the drawings, any suitable power and data wires or the like may be coupled between the latch and ejector 210 and connector 141 and corresponding portions of the apparatus 10, such as a power supply, computer, and/or the like. The connectors 140, 141 may be low friction connectors constructed so that the drawer connector 140 is inherently guided into the mating cart connector 141 with little to no effort, for example, 0.1 to 0.4 lbs of force and, more specifically about 0.2 lbs of force. Also, the low friction connectors 140, 141 are constructed so that the drawer connector 140 is easily disengaged from the mating cart connector 141 when the drawer 100 is unlatched from the housing of the apparatus 10.

The backplane 180 may be communicated in any suitable manner to the computer 50, which is in communication with the connectors 141 and is programmed in accord with the array of compartments 16. Accordingly, the locations of the drawers 100 in the compartments 16 can be communicated to and stored in the computer 50 in any suitable manner.

The apparatus 10 also may include a guide pin 250 that may be coupled to the backplane 180 to align the drawer 100 with respect to the backplane 180 for good alignment of the connectors 140, 141 and the latch and ejector 210 with respect to the latch aperture 116. For example, the guide pin 250 may extend through the backplane 180 and a fastener 252 may fasten the guide pin 250 to the backplane 180. The guide pin 250 is adapted for cooperation with the guide pin passage 135 of the drawer 100.

In use, the drawer 100 may be pushed toward the backplane 180 wherein the latch member 218 contacts a rear wall of the drawer 100, for example, the rear surface of the rear cover 107 of the drawer 100. Also, the guide pin 250 engages the guide pin passage 135, and the connectors 140, 141 eventually engage one another. The cam surface 117 of the rear cover 107 may initially engage an angled surface at the bayonet end of the latch member 218, and the guide pin 250 may engage the corresponding passage 135 to stably pilot the drawer 100 for good connector alignment and engagement.

As the drawer 100 continues advancing and nears its closed position, the connectors 140, 141 operatively engage. At this point, the computer 50 (FIG. 1) recognizes the drawer 100 using, for example, any suitable plug-and-play utility like USB, or the like. In other words, the connectors 140, 141 may be configured as part of a drawer presence detection device wherein the computer 50 recognizes that the drawer 100 is engaged to the apparatus 10 when the connection between the connectors 140, 141 is made. For example, the computer 50 may periodically poll the memory devices 142 (FIG. 2A) via the connectors 140, 141 and read serial numbers and other data of the memory devices 142.

Figure 6:
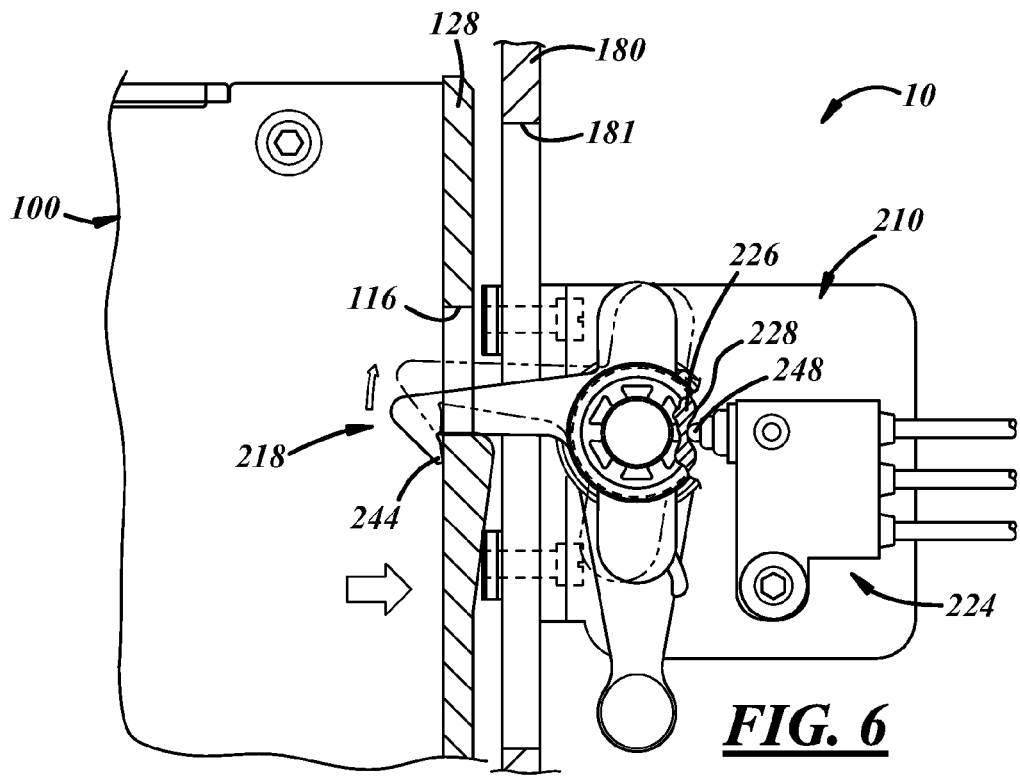
FIG. 6 is a fragmentary side view of a portion of the apparatus of FIG. 1, illustrating the electromechanical latch and ejector of FIG. 3 in a latched position with respect to one of the drawers of FIG. 1.

As shown in FIG. 6, the drawer 100 may continue to be pushed toward the backplane 180 (as shown by the large arrow) wherein the latch member 218 pivots (as indicated by the little arrow, and as shown in hidden lines) from its home position (shown in FIG. 5), and the bayonet end of the latch member 218 projects through the latch aperture 116 until the barb 244 clears a rear inside surface of the drawer 100 adjacent the aperture 116. At that point, the latch member 218 can drop or move into a latched position with the barb 244 engaged with the base wall 128 of the rear cover 107 of the drawer 100. The drawer 100 will remain in the latched state until a signal is sent from the computer 50 (FIG. 1) of the apparatus 10 to the actuator 214 to unlatch the drawer 100.

The home position and latched position of the latch member 218 may be the same. In the home position, the reference 228 may be in a home position with respect to the sensor 224. More specifically, the plunger 248 may be engaged in the detent in the ejector hub 226 as shown.

In operation, an attendant may use the touchscreen 14 (FIG. 1) in communication with the computer 50 (FIG. 1) to request unlatching of the drawer 100 and, in turn, the computer 50 may send any suitable signal(s) to the latch and ejector 210, for example, via a dedicated output for each drawer via an input/output rack of the apparatus 10. When the actuator 210 is energized, the ejector and latch members 216, 218 rotate.

With reference to FIG. 6, the latch member 218 rotates so that the barb 244 of the latch member 218 disengages from the base 128 of the rear cover 107. The bayonet end of the latch member 218 may contact the upper boundary of the aperture 116 at the base 128 but, given the relative motion between the members 216, 218, the ejector member 216 may continue to rotate.

Figure 7:
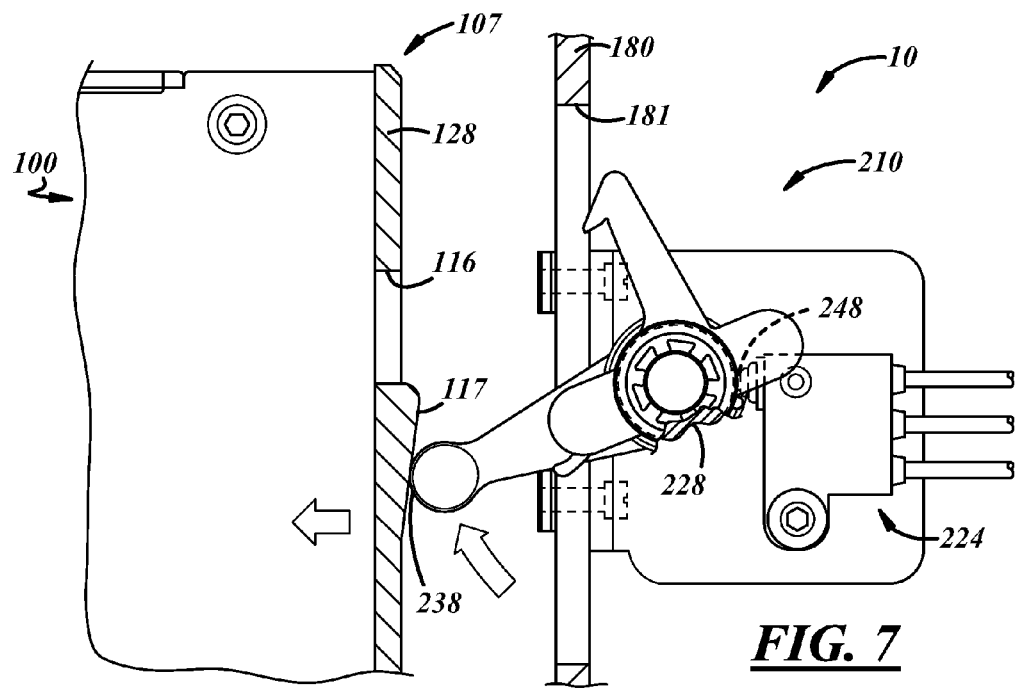
FIG. 7 is a fragmentary side view of a portion of the apparatus of FIG. 1, illustrating the electromechanical latch and ejector of FIG. 3 in an unlatched ejection position with respect to one of the drawers of FIG. 1.

Accordingly, as shown in FIG. 7, the ejector member 216 rotates into and through the backplane aperture 181 and contacts the drawer 100, while the latch member 218 rotates out of and through the backplane aperture 181. More specifically, the end 238 of the ejector member 216 contacts the rear surface of the rear cover 107 including the cam surface 117. The engagement of the ejector member 216 with the drawer 100 causes ejection or outward displacement of the drawer 100 relative to the backplane 180. Also, the position reference 228 has rotated with respect to the sensor 224, wherein the sensor 224 is in such a state so as to ensure that power is continuously supplied to the actuator 214 until the position reference 228 and the sensor 224 are realigned. For example, the plunger 248 of the sensor 224 may be depressed so as to activate the sensor 224 in a closed-loop configuration to complete a circuit so that power continues to be supplied to the actuator 214.

Figure 8:
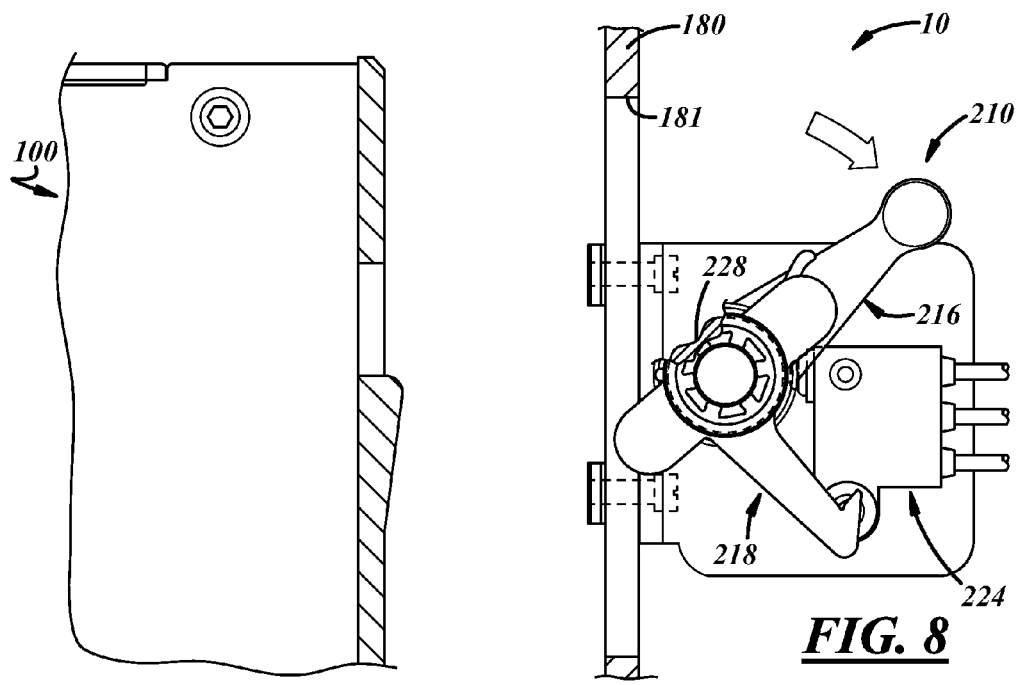
FIG. 8 is a fragmentary side view of a portion of the apparatus of FIG. 1, illustrating the electromechanical latch and ejector of FIG. 3 in a position rotated over half-way of a full revolution.

As shown in FIG. 8, even though the drawer 100 has been ejected, the ejector and latch members 216, 218 continue their rotation over a full revolution back toward their home positions. The full rotation can be accomplished in any suitable manner but, in one example, the sensor 224 may be activated so that power continues to flow to the actuator 214 in a closed circuit until the positional reference 228 and the sensor 224 realign to open the circuit and de-energize the actuator 214 as shown in FIG. 3. The computer 50 (FIG. 1) senses disengagement of the electrical connectors 140, 141 using, for example, any suitable plug-and-play utility like USB, or the like, or in any other suitable manner.

Figure 9:
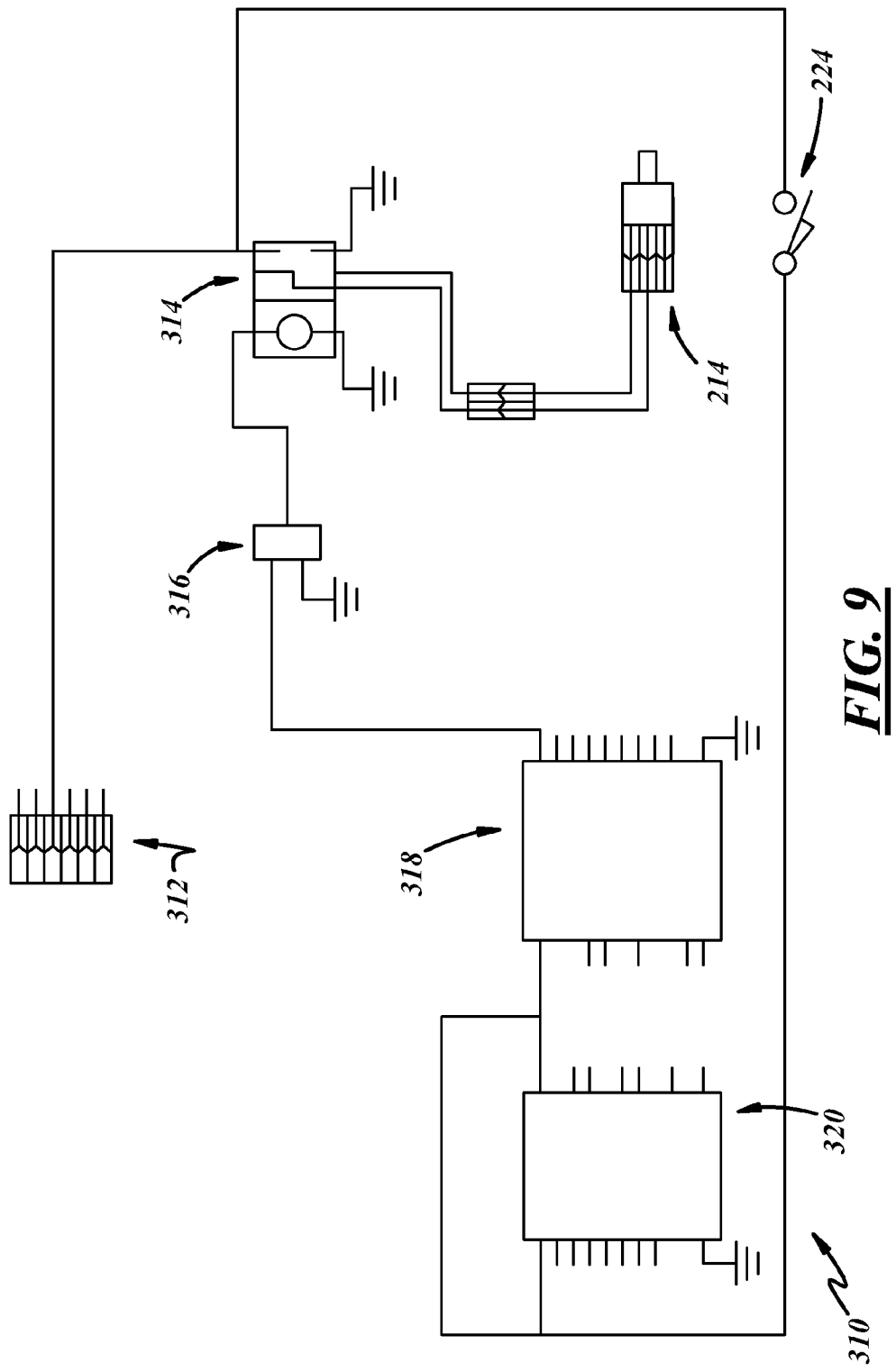
FIG. 9 is an example electrical schematic for a portion of the apparatus of FIG. 1.

As shown in FIG. 9, each drawer may be associated with an electrical configuration 310 that may include a power supply 312, the actuator 214, and the sensor 224. The power supply 312 may include a direct connection to the batteries 18 of FIG. 1 or an indirection connection thereto via a power distribution block or the like. Power may be communicated to the actuator 214 via a relay 314 that may include a connection to the power supply 312 and one end of the sensor 224. The sensor 224 may have ends or poles across which the sensor may be activated to connect the poles. In the illustrated embodiment, the sensor 224 may be a normally open switch, but a normally closed switch instead may be used. The relay 314 may be a PANASONIC brand relay, model TX2-5V available from Matsushita of Japan. A drive signal may be communicated to the relay 314 via a load driver 316 that may include an output connection to an input on the relay 314, a ground connection, and an input connection. The load driver 316 may be an ON SEMICONDUCTOR brand load driver, model NUD3105 available from Semiconductor Components Industries of Phoenix, Ariz. A control signal may be communicated to the load driver 316 via a digital chip 318 that may include a logical high output connected to the input of the load driver 316, a ground, and a power input coupled to another end of the sensor 224. The chip 318 may be in communication with another digital chip 320 that may include a power input coupled to the other side of the sensor 224, a ground, and a sensor input coupled to the other side of the sensor 224. The chip 318 may be an NXP brand shift register with latches, model 74HC595, and the other chip 320 may be an NXP brand shift register, model 74HC165, both available from NXP Semiconductors of Eindhoven, Netherlands.

The electromechanical latch and ejector 210 is actuated by the logical high output from the chip 318 firing or powering the load driver 316. Accordingly, the load driver 316 activates the relay 314 to power to the actuator 214 causing the ejector member 216 to rotate and, thus, actuate the sensor 224 away from its home position or condition to close the circuit and power the chips 318, 320. The other chip 320 is used to monitor the sensor 224. When the ejector member 216 rotates for one revolution and returns to its home position, the sensor 224 also returns to its home position or condition by virtue of the interaction between the ejector member 216 and the sensor 224. Accordingly, the circuit opens and power is dropped from the load driver 316 thereby deactivating the relay 314. When the relay 314 is deactivated, the power leads to the actuator 214 are shorted together to brake the actuator 214 quickly. Those of ordinary skill in the art will recognize that one or more aspects of the activation and deactivation of the electromechanical latch and ejector 210 may be replaced or supplemented by software code settings of one or both of the chips 318, 320 or elsewhere in the system.

In general, the components of the apparatus 10 may be manufactured according to techniques known to those skilled in the art, including molding, machining, stamping, and the like. Also, the apparatus 10 may be assembled according to known techniques. Likewise, any suitable materials can be used in making the components, such as metals, composites, acetal polymers or other polymeric materials, and the like.

As used in the sections above and claims below, the terms "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components, elements, or items. Similarly, when introducing elements of the invention or the example embodiments thereof, the articles "a," "an," "the," and "the" are intended to mean that there are one or more of the elements. Moreover, directional words such as front, rear, top, bottom, upper, lower, radial, circumferential, axial, lateral, longitudinal, vertical, horizontal, transverse, and/or the like are employed by way of description and not limitation. Other terms are to be construed using their broadest reasonable meaning unless they are used in a context that requires a different interpretation.

Finally, the foregoing description is not a definition of the invention, but is a description of one or more examples of illustrative embodiments of the invention. The statements contained in the foregoing description relate to the particular examples and are not to be construed as limitations on the scope of the invention as claimed below or on the definition of terminology used in the claims, except where terminology is expressly defined above. And although the present invention has been disclosed using a limited number of examples, many other examples are possible and it is not intended herein to mention all of the possible manifestations of the invention. In fact, other modifications, variations, forms, ramifications, substitutions, and/or equivalents will become apparent to those skilled in the art in view of the foregoing description. The present invention is intended to embrace such forms, ramifications, modifications, variations, substitutions, and/or equivalents as fall within the spirit and broad scope of the following claims. In other words, the present invention encompasses many substitutions or equivalents of limitations recited in the following claims. For example, the materials, sizes, and shapes, described above could be readily modified or substituted with other similar materials, sizes, shapes, and/or the like. Therefore, the invention is not limited to the particular examples of illustrative embodiments disclosed herein, but instead is defined solely by the claims below.

What is claimed is:

1. An electromechanical latch and elector to unlatch and elect a drawer, the latch and elector comprising:
   an electrical actuator to produce revolutionary rotational motion;
   an ejector member coupled to the actuator for revolutionary rotation; and
   a latch member coupled to at least one of the ejector member or the actuator for revolutionary rotation,
   wherein the electromechanical latch and ejector unlatches and ejects the drawer and wherein the ejector member includes an ejector hub having angularly spaced stops with an angular space therebetween, and the latch member includes a latch hub disposed generally axially adjacent the ejector hub and having an axially extending projection disposed in the angular space between the stops of the ejector hub.

2. The electromechanical latch and ejector of claim 1, further comprising a torsional spring coupled between the ejector member and the latch member and having one end engaged to the ejector member and another end engaged to the latch member.

3. An apparatus, comprising:
   a backplane having a backplane aperture therethrough;
   a drawer disposed on one side of the backplane and including a rear wall having a drawer aperture therethrough; and
   an electromechanical latch and ejector disposed on another side of the backplane to selectively couple the drawer to the backplane and selectively eject the drawer away from the backplane and including:

a latch member extending through the backplane aperture and into the drawer aperture when the latch member latches the drawer to the backplane, and an ejector member rotatable through the backplane aperture and against the rear wall of the drawer when the ejector member ejects the drawer away from the backplane, wherein the electromechanical latch and ejector further includes an electrical actuator to produce revolutionary rotational motion, wherein the ejector member is coupled to the actuator for revolutionary rotation, and the latch member is coupled to the actuator for revolutionary rotation and with respect to the ejector member via a rotary lost motion connection.

4. The apparatus of claim 3, wherein the electrical actuator is operable to rotate the ejector and latch members over a complete revolution to unlatch and eject the drawer.

5. The apparatus of claim 3, wherein the latch member is pivotably carried on a portion of the ejector member.

6. The apparatus of claim 3, further comprising a torsional spring coupled between the ejector member and the latch member and having one end engaged to the ejector member and another end engaged to the latch member, and wherein the ejector member includes an ejector hub having angularly spaced stops with an angular space therebetween, and the latch member includes a latch hub disposed generally axially adjacent the ejector hub and having an axially extending projection disposed in the angular space between the stops of the ejector hub.

7. An electromechanical latch and ejector to unlatch and eject a drawer, comprising:
an electrical actuator to produce revolutionary rotational motion;
an ejector member rotationally fixed with respect to the actuator for revolutionary rotation;
a latch member coupled to at least one of the ejector member or the actuator for revolutionary rotation;
wherein the electrical actuator is operable to rotate the ejector and latch members over a complete revolution to unlatch and eject the drawer and wherein the latch member is pivotably coupled with respect to the ejector member via a rotary lost motion connection.

8. The electromechanical latch and ejector of claim 7, further comprising:
a spring operatively coupled to the ejector member and the latch member to bias the latch member to a normal latch position with respect to the ejector member; and
a sensor operatively coupled to the ejector member to provide an indication of a rotational position of the ejector member.

9. The electromechanical latch and ejector of claim 7, wherein the latch member is pivotably carried on a portion of the ejector member.

10. An apparatus, comprising:
a drawer; and
an electromechanical latch and ejector to selectively unlatch and eject the drawer and including:
a latch including a latch arm to latch to the drawer in a latched position,
an ejector including an ejector arm to eject the drawer in an unlatched position, and
an electrical actuator coupled to the latch and the ejector and operable to rotate the latch and the ejector to unlatch and eject the drawer;
a backplane having a backplane aperture therethrough, wherein the drawer is disposed on one side of the backplane and has a drawer aperture therethrough, the electromechanical latch and ejector is disposed on another side of the backplane to selectively couple the drawer to the backplane and selectively eject the drawer away from the backplane, the latch extends through the backplane aperture and into the drawer aperture when the latch latches the drawer to the backplane.

11. The apparatus of claim 10, wherein the latch member and the ejector member are separate components with the latch member being coupled with respect to the ejector member via a rotary lost motion connection.

12. The electromechanical latch and ejector of claim 11, further comprising:
a spring coupled to the ejector member and the latch member to bias the latch member to a normal latch position with respect to the ejector member.

13. The apparatus of claim 10, further comprising:
a sensor operatively coupled to at least one of the actuator, the ejector member, or the latch member, wherein the sensor provides an indication of a rotational position of at least one of the actuator, the ejector member, or the latch member.

14. The apparatus of claim 13, wherein at least one of the actuator, the ejector member, or the latch member includes a rotational position reference and the sensor includes a portion for operable coupling to the rotational position reference.

15. The apparatus of claim 14, wherein the rotational position reference is a detent and the sensor is electromechanical and includes a translatable plunger.

16. The apparatus of claim 10, wherein the actuator includes an electric motor having an output shaft, the ejector member is rotationally fixed with respect to the output shaft, and the latch member is pivotably coupled with respect to the output shaft.

17. The apparatus of claim 16, wherein the latch member is pivotably carried on a portion of the ejector member.

18. The apparatus of claim 10, further comprising:
a mounting bracket having a flange, wherein the electrical actuator is carried by the bracket on one side of the flange, and the ejector member and the latch member are disposed on another side of the flange.

19. The apparatus of claim 10, wherein the ejector member and the latch member are unitary, the latch member includes a latch arm that has a bayonet end and that resiliently deflects for latching engagement with another object.

20. The apparatus of claim 10, wherein the electrical actuator is operable to rotate the ejector and latch members over a complete revolution to unlatch and eject the drawer.

21. The electromechanical latch and ejector of claim 10, further comprising:
a mounting bracket having a flange, wherein the electrical actuator is carried by the bracket on one side of the flange, and the ejector member and the latch member are disposed on another side of the flange.

22. The apparatus of claim 10, further comprising:
a sensor operatively coupled to the ejector member to provide an indication of a rotational position of the ejector member;
a powered relay coupled to one end of the sensor;
a load driver to communicate a drive signal to the relay;
a digital chip to communicate a control signal to the load driver and having a power input coupled to an other end of the sensor; and
an other digital chip having a sensor input coupled to the other end of the sensor to monitor rotation of the ejector member and a power input also coupled to the other end of the sensor.

23. The electromechanical latch and ejector of claim 22 wherein a logical high output from the digital chip powers the load driver, wherein the load driver activates the relay to power the actuator and cause the ejector member to rotate, and, thus, cause actuation of the sensor to close and power the other digital chip.

24. The electromechanical latch and ejector of claim 23 wherein the ejector member rotates for one revolution and returns to its home position and, concomitantly, the sensor returns to its home condition such that power is dropped from the load driver to deactivate the relay and thereby short power leads to the actuator to brake the actuator.

25. The apparatus of claim 10, wherein the electromechanical latch and ejector is coupled to a rear surface of the backplane.

26. The apparatus of claim 10, wherein the ejector and the latch are separate components, with the latch being coupled with respect to the ejector via a rotary lost motion connection.

27. An apparatus, comprising:
a drawer; and
an electromechanical latch and ejector to selectively unlatch and eject the drawer and including:
a latch including a latch arm to latch to the drawer in a latched position,
an ejector including an ejector arm to eject the drawer in an unlatched position, and
an electrical actuator coupled to the latch and the ejector and operable to rotate the latch and the ejector to unlatch and eject the drawer, wherein the ejector and the latch are unitary.

28. The apparatus of claim 27 wherein the electromechanical latch and ejector is coupled to a rear surface of the backplane.

29. The apparatus of claim 27 further comprising a mounting bracket having a first flange coupled to the backplane, and a second flange wherein the electric motor is carried by the bracket on one side of the second flange, and the ejector member and the latch member are disposed on another side of the second flange.

* * * * *